United States Patent [19]

Van den Berg et al.

[11] Plant 4,728

[45] May 26, 1981

[54] KALANCHOE PLANT

[75] Inventors: Cornelis P. Van den Berg; James C. Mikkelsen, both of Ashtabula, Ohio

[73] Assignee: Mikkelsens Inc., Ashtabula, Ohio

[21] Appl. No.: 134,127

[22] Filed: Mar. 26, 1980

[51] Int. Cl.[3] ..... A01H 5/00

[52] U.S. Cl. ..... Plt./68

[58] Field of Search ..... Plt./68

*Primary Examiner*—James R. Feyrer

*Attorney, Agent, or Firm*—Schwartz, Jeffery, Schwaab, Mack, Blumenthal & Koch

[57] ABSTRACT

A new kalanchoe plant referred to by the cultivar name Firefly, and characterized by its large, bright yellow and well clustered flowers; vigorous plant growth; relatively large leaves and strong peduncles, and by its adaptability to growth in varying size pots and to treatment with growth regulators.

1 Drawing Figure

1

The present invention relates to a new and distinctive cultivar of Kalanchoe plant, botanically known as *Kalanchoe blossfeldiana Poelln.* and referred to by the cultivar name Firefly. The new cultivar was developed by us through controlled breeding by self-pollinating Mikkelsen seedling No. 75-101, an unpatented cultivar. Asexual reproduction by stem cuttings has shown that the unique features of the new cultivar are stabilized and are reproduced true to type in successive propagations.

The following characteristics distinguish the new kalanchoe from both its parent varieties and other cultivated kalanchoes of this type known and used in the floriculture industry:

1. Firefly was selected specifically for the good keeping quality of the foliage and the flowers, both in the greenhouse and in the home.
2. Branching, with or without pinching, is better than most vegetatively propagated yellow kalanchoes currently on the market.
3. Plant growth is vigorous, with relatively large leaves and strong peduncles.
4. Proper scheduling makes new cultivar suitable for production in 10 cm. to 15 cm. and larger pots.
5. Elongation of the lower nodes can be decreased by spraying with B9 as soon as the cutting is rooted.
6. After flowering initiation, plants must be treated with B9 in all seasons in order to reduce peduncle elongation.
7. Flowering time is 10 weeks in summer to approximately 14 weeks in winter after start of short days.
8. Cultivar exhibits large, bright yellow flowers, which are well clustered.

The accompanying colored photograph illustrates the overall appearance and color of Firefly. The photograph is a top view, and shows the colors as true as it is reasonably possible to obtain in a colored reproduction of this type.

The following is a detailed description of Firefly based on plants produced under commercial practices in the greenhouses of Mikkelsens Inc., Ashtabula, Ohio Color references are made to the Royal Horticultural Society Colour Chart except where general terms of ordinary dictionary significance are used.

Parentage:

A controlled self-pollination of Mikkelsen seedling No. 75-101.

2

Propagation:

(A) *Type cutting.*—Short tip cutting, with stems up to 2 cm. long.

(B) *Time to root.*—10 days at 21° C. summer, 14 days at 21° C. winter.

(C) *Rooting habit.*—Many very fine roots, fibrous.

Plant description:

(A) *Form.*—Upright growth; compactness depends on growth regulator applications. Growing and scheduling practices can result either in a small plant in a 10 cm. pot or a larger plant in a 15 cm. pot.

(B) *Habit of growth.*—Rate of growth moderate to fast for this type of plant. Under optimum conditions, side shoots are generally formed at every node.

(C) *Foliage description.*—Leaves simple, opposite; frequently, leaves are slightly twisted along the main vein. (1) Size: Average full grown leaf of a flowering plant in a 4" pot is 120 mm. long × 75 mm. wide. Plants in larger pots have leaf sizes up to 150 mm. long × 110 mm. wide. (2) Shape: Elliptic, apex obtuse, base obtuse to very slightly attenuate. (3) Texture: Glabrous, coriaceous, succulent. (4) Margin: Sinuate to crenate. (5) Color: Young foliage top side green 137A, under side green 137B-C. Mature foliage top side slightly darker than green 137A, under side green 137B-C.

Flowering description:

(A) *Inflorescence of each shoot.*—Is formed by dichotomous branching, starting with opening of terminal flower of main axis, followed by terminal flowers of the side branches in the inflorescence. Opening of new buds will continue for two months or more. Individual flowers last two weeks or more after opening.

(B) *Natural flowering.*—Season is late January. Flowering time under controlled daylength at 20° C. in summer is 10 weeks; in winter at 20° C., 15 weeks. Flowering time depends on temperature, light intensity and other growing conditions.

(C) *Flower bud description.*—Generally oblong, up to 12 mm. long, developing to tubular as flower petals mature, sheathed with four green sepals; corolla at maturity 10 mm. long.

(D) *Flowers borne.*—Compound dichasial cyme on strong peduncles, with the primary peduncle being up to 5 mm. in diameter. Peduncle length depends on growing conditions and B9 application; pedicels up to 10 mm. long.

(E) *Quantity of flowers.*—Floriferous; main axis has 100 or more flowers, side shoots 50 or more flowers, with new buds continuing to develop.

(F) *Petals.*—(1) Shape: Nearly round, top cuspidate. (2) Color: Top side when opening yellow 11A, fading to yellow-orange 16B, under side yellow 10B. (3) Number of petals: Four (4), united in corolla, salverform; petals 7 mm. in diameter, total flower diameter 16 mm.

(G) *Reproductive organs.*—(1) Stamens: Eight (8) in number. (a) Anther shape: flat, elliptical, color yellow. (b) Filament color: light green. (c) Pollen color: yellow. (2) Pistils: (a) Stigma shape: flat, crystalline, color greenish white. (b) Style color: light green. (c) Ovaries: 4 celled, 6 mm. long, green in color.

Disease resistance:

No known kalanchoe diseases observed to date. The cultivar is highly resistant to mildew.

We claim:

1. A new and distinct cultivar of kalanchoe known by the cultivar name Firefly, as described and illustrated, and particularly characterized by its large, bright yellow and well clustered flowers; vigorous plant growth relatively large leaves and strong peduncles, and by its adaptability to growth in varying size pots and to treatment with growth regulators.

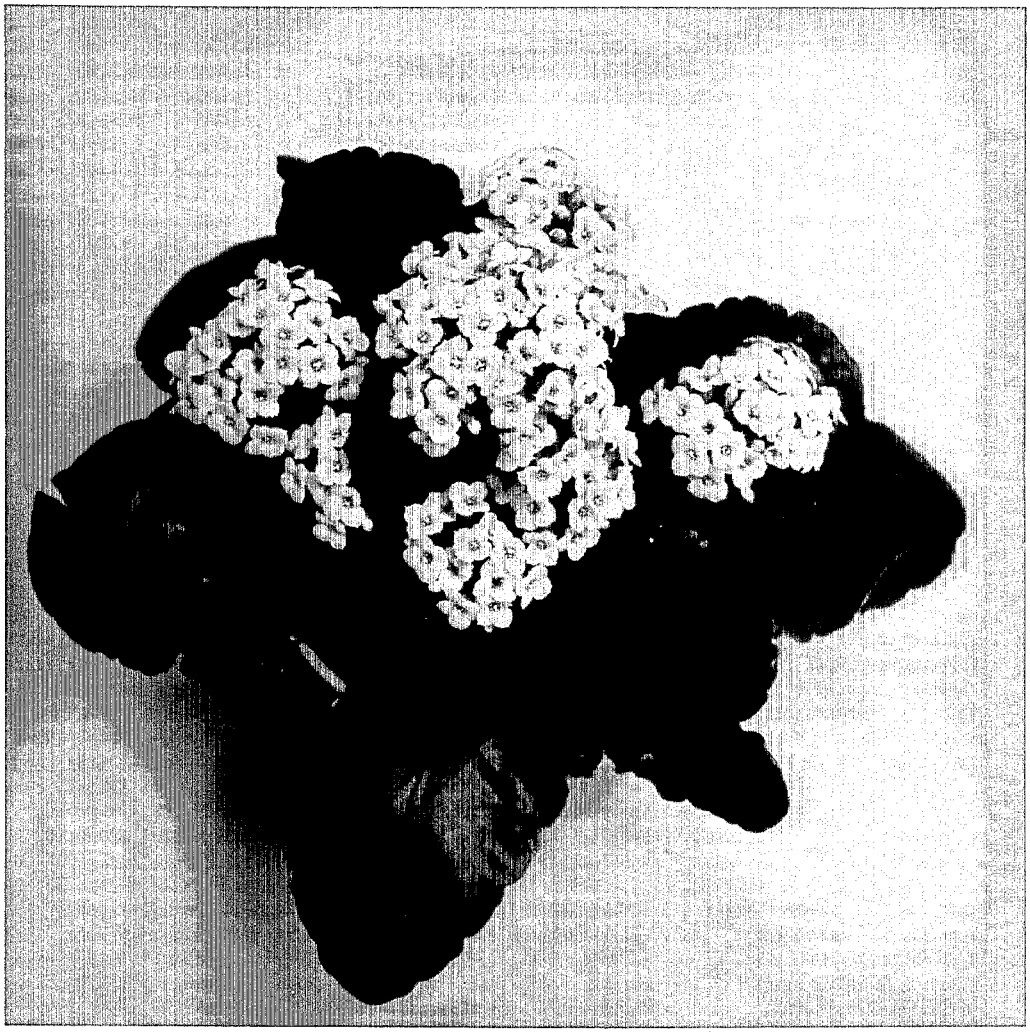

* * * * *